US008778314B2

(12) United States Patent
Jones et al.

(10) Patent No.: US 8,778,314 B2
(45) Date of Patent: Jul. 15, 2014

(54) CO-POLYMERS IN HAIR STYLING APPLICATIONS

(75) Inventors: Debra L. Jones, Selby (GB); Sylvie L. Reid, Leeds (GB); Sean P. N. Rouse, Kingston-Upon-Hull (GB)

(73) Assignee: Croda International PLC, Goole, North Humberside (GB)

( * ) Notice: Subject to any disclaimer, the term of this patent is extended or adjusted under 35 U.S.C. 154(b) by 756 days.

(21) Appl. No.: 12/309,200

(22) PCT Filed: Jul. 16, 2007

(86) PCT No.: PCT/GB2007/002666
§ 371 (c)(1),
(2), (4) Date: Jul. 23, 2009

(87) PCT Pub. No.: WO2008/009907
PCT Pub. Date: Jan. 24, 2008

(65) Prior Publication Data
US 2009/0311205 A1 Dec. 17, 2009

(30) Foreign Application Priority Data

Jul. 19, 2006 (GB) .................................. 0614314.3

(51) Int. Cl.
*A61K 8/00* (2006.01)
*A61K 8/18* (2006.01)
*A61Q 17/04* (2006.01)
*A61K 9/00* (2006.01)

(52) U.S. Cl.
USPC ........................................... 424/59; 424/400

(58) Field of Classification Search
USPC .................................... 424/59, 400
See application file for complete search history.

(56) References Cited

U.S. PATENT DOCUMENTS

| 2,579,986 | A | | 2/1950 | Vaterrodt et al. |
| 6,056,945 | A | * | 5/2000 | Cauwet-Martin et al. ... 424/70.1 |
| 2005/0232886 | A1 | | 10/2005 | Walter et al. |

FOREIGN PATENT DOCUMENTS

| EP | 0057728 | 5/1986 |
| EP | 0583973 | 2/1994 |
| GB | 1361029 | 7/1974 |
| JP | 59172136 | 9/1984 |
| JP | 04-334312 | 11/1992 |
| JP | 2000282382 | 10/2000 |
| JP | 2003261623 | 9/2003 |
| JP | 2004155937 | 6/2004 |
| JP | 2004-277384 | 10/2004 |
| SU | 550408 | 5/1977 |
| WO | WO 94/02112 | 2/1994 |
| WO | 00/78269 | 12/2000 |

OTHER PUBLICATIONS

International Search Report for PCT/GB2007/002666 dated Nov. 12, 2007.
Official Action mailed Oct. 1, 2013 for corresponding Japanese Application No. 2009-520042 (references cited on p. 2).
Official Action mailed Oct. 30, 2012 in corresponding Japanese Application No. 2009-520042.
Official Action mailed Oct. 19, 2006 in priority United Kingdom Application No. 0614314.3.

* cited by examiner

*Primary Examiner* — Mina Haghighatian
*Assistant Examiner* — Luke Karpinski
(74) *Attorney, Agent, or Firm* — Jones Day

(57) ABSTRACT

Hair is treated with a copolymer of an unsaturated ester and a styrene sulphonate monomer to reducing damage to hair caused by subsequent heat treatment. The styrene sulphonate monomer is desirably sodium styrene sulphonate and the unsaturated ester is desirably of an unsaturated monocarboxylic acid, such as (meth)acrylic acid, or dicarboxylic acid, such as maleic acid, and an alcohol, desirably an alkoxylated alcohol such as ethoxylated lanolin alcohol. Formulations for hair treatment generally include from about 0.5 to about 25% by weight of the copolymer.

29 Claims, 2 Drawing Sheets

CO-POLYMERS IN HAIR STYLING APPLICATIONS

CROSS REFERENCE TO RELATED APPLICATION

Figure 1:
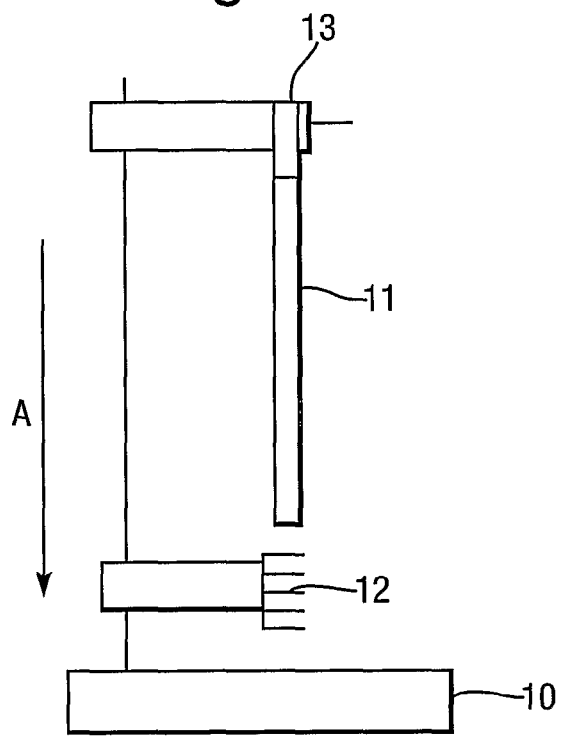

This application is the National Phase application of International Application No. PCT/GB2007/002666, filed Jul. 16, 2007, which designates the United States and was published in English. This application, in its entirety, is incorporated herein by reference.

The present invention relates to hair care compositions and particularly to the use of copolymers of unsaturated esters and styrene sulphonates to improve the thermal protection properties of hair styling formulations.

Heat styling, particularly using blow dryers, hair straighteners or curling devices which heat the hair during styling, is prevalent amongst consumers. Unfortunately, heat styling can dry out and damage hair particularly by subjecting the hair to too much heat. For example, hair can be overdryed by holding a blow dryer too close to the hair, or by holding a blow dryer or curling device too long at a particular spot of the hair. The overheating causes moisture to be driven out of the hair so that the hair becomes brittle and more susceptible to cracking. In addition, overheating in heat styling can cause physical damage to the hair, particularly by raising the cuticles and/or creating blisters on individual hair fibres, thus causing increased friction between the hair fibres, making it more difficult to comb, requiring increased force to comb the hair, leading to wear to the outer surface of the hair and potentially cracks and breaks in the hair.

Current approaches to protecting hair from such thermal damage include the use of silicone containing compounds such as polydimethicanol, cyclopentasiloxane and amodimethicone (Dow Corning), co-polymers of vinyl containing monomers such as copolymers of vinyl pyrrolidone and dimethyl aminopropyl methacrylate (Styleze CC-10, ISP Corp) and sodium polystyrene sulphonate (Flexan II, National Starch).

Unsaturated esters have been reported widely as being beneficial in personal care applications, however they have no reported benefit for thermal protection of hair.

We have unexpectedly discovered that co-polymers of unsaturated esters and styrene sulphonate monomers can provide good thermal protection in hair treatment formulations and in particular can have significantly superior thermal protection properties to conventional polymers such as sodium polystyrene sulphonate.

Accordingly the present invention provides a method of treating hair wherein a composition comprising a copolymer of an unsaturated ester and a styrene sulphonate as an agent to reducing damage to hair caused by heat treatment or styling is applied to the hair, which is subsequently styled or otherwise subjected to heat treatment.

The invention includes a hair care composition, particularly for the pre-treatment of hair before heating and styling, which composition includes a copolymer of an unsaturated ester and a styrene sulphonate as an agent to reducing damage to hair caused by heat treatment or styling.

Certain of the copolymers used in the method and composition of the invention are believed to be novel as compounds in their own right and the invention accordingly includes a copolymer of an unsaturated ester of a (poly)alkoxylated alcohol and a carboxylic acid and a styrene sulphonate monomer.

The copolymer used in the method and composition of this invention is a copolymer of a styrene sulphonate monomer and an unsaturated ester.

Generally the styrene sulphonate monomer will be styrene sulphonate, most commonly in neutralised or salt form, particularly the alkali metal or amine salt form, and especially conveniently as (the readily commercially available) sodium styrene sulphonate.

The unsaturated esters are generally esters of unsaturated carboxylic acids and alcohols. The unsaturated acids are ethylenically unsaturated, particularly α,β-unsaturated carboxylic acids.

The unsaturated carboxylic acid can be a dicarboxylic acid; suitable examples including maleic, fumaric, itaconic, citraconic, and mesaconic acids, or combinations of two or more of these, with maleic acid being particularly suitable and preferred. Alternatively, the unsaturated carboxylic acid can be a monocarboxylic acid; suitable examples including acrylic, methacrylic, crotonic, 3-methylcrotonic, and 3-butenoic acids, or combinations of two or more of these, with (meth)acrylic acid being particularly suitable and preferred. If desired, mixtures or combinations of these types of acid may be used.

A wide variety of alcohols can be used to form the unsaturated ester. Suitable types of alcohols include straight chain alcohols, branched chain alcohols, cyclic alcohols, aromatic alcohols, sterols, stanols, alcohols derived from woolgrease such as lanolin alcohols, diols, polyols, and mixtures or combinations of these.

As the lubricating properties of the copolymers are at least in part contributed by the alcohol residue in the ester it is generally desirable to use relatively fatty alcohols e.g. those having more than about 12 and up to about 35, particularly from 14 to 33 carbon atoms such as the sterols, which are based on the 17-C steroid framework and typically have about 27 carbon atoms, stanols (hydrogenated sterols), which typically have about 27 carbon atoms, and alcohols derived from woolgrease, such as lanolin alcohols, which typically have from 14 to 33 carbon atoms, mentioned above.

We have obtained particularly good results using alkoxylated, particularly polyalkoxylated, alcohols. when the alcohol is (poly)alkoxylated the (poly)alkoxylating moiety is desirably oxyethylene, polyoxyethylene, oxypropylene, polyoxypropylene or a combination of these. The degree of alkoxylation in such (poly)alkoxylated alcohols is typically from 1 to about 100, more usually from 2 to about 50, and particularly about 40, moles of the alkoxylating moiety(s) per mole of alcohol.

We have found that (poly)alkoxylated alcohols provide esters with improved aqueous solubility and this benefits both synthesis of copolymers (conveniently carried out in aqueous solution) and their performance when used in the method and compositions of this invention. We have obtained particularly good results using ethoxylated lanolin alcohols in the unsaturated esters and this accordingly forms a particularly desirable aspect of the invention.

The chemical composition of the unsaturated ester/sodium polystyrene sulphonate of the present invention can be considered in two parts. An unsaturated ester which is then co-polymerised with sodium styrene sulphonate to produce the unsaturated ester/sodium polystyrene sulphonate of the present invention.

Particularly useful unsaturated esters are those based on unsaturated, particularly α,β-unsaturated, monocarboxylic acids of the formula (I) or unsaturated, particularly α,β-unsaturated, dicarboxylic acids of the formula (II):

$$R^1O_2CR^2 \tag{I}$$

$$R^1O_2CR^4CO_2R^5 \tag{II}$$

$R^1$ is the residue of an alcohol $R^1OH$;
$R^2$ is an unsaturated monovalent radical of the monocarboxylic acid $HO_2CR^2$;
$R^4$ is an unsaturated divalent radical of the dicarboxylic acid $HO_2CR^4CO_2H$;
$R^5$ is H or independently a group as defined for $R^1$.

Within these formulae, the copolymer compounds of the invention incorporate residues of unsaturated esters of the formulae (Ia) and (IIa):

$$R^{1'}O_2CR^2 \tag{Ia}$$

$$R^1O_2CR^4CO_2R^{5'} \tag{IIa}$$

where
$R^{1'}$ is the (poly)alkoxylated residue of a (poly)alkoxylated alcohol $R^{1'}OH$;
$R^{5'}$ is H or independently a group as defined for $R^{1'}$; and
$R^2$ and $R^4$ are respectively as defined for formula (I) and formula (II) respectively.

These unsaturated esters can be copolymerised with styrene sulphonate monomers, particularly sodium styrene sulphonate, by synthetic methods known to practitioners skilled in the art, usually by addition polymerisation of the ethylenic unsaturation in the styrene sulphonate with the unsaturation on the unsaturated ester.

The copolymers used in the method and composition of the invention can be represented by the formulae (III) and (IV):

$$(R^1O_2CR^{2'})_{m1}(R^3)_{n1} \tag{III}$$

$$(R^1O_2C(R^5O_2C)R^{4'})_{m2}(R^3)_{n2} \tag{IV}$$

where
$R^1$ and $R^5$ are as defined in formula (II) above
$R^3$ is the residue of a styrene sulphonate monomer, particularly sodium styrene sulphonate;
$R^{2'}$ is the residue of a (copolymerised) unsaturated monovalent radical of the monocarboxylic acid $HO_2CR^2$; (where $R^2$ is an unsaturated monovalent radical)
$R^{4'}$ is the residue of a (copolymerised) unsaturated divalent radical of the dicarboxylic acid $HO_2CR^4CO_2H$ (where $R^4$ is an unsaturated divalent radical); and
m1, n1, m2 and n2 are the numbers of repeats of the respective co-monomers in the copolymer.

The copolymers of the invention can be represented by the formulae (IIIa) and (IVa):

$$(R^{1'}O_2CR^{2'})_{m1}(R^3)_{n1} \tag{IIIa}$$

$$(R^1O_2C(R^{5'}O_2C)R^{4'})_{m2}(R^3)_{n2} \tag{IVa}$$

where
$R^{1'}$ and $R^{5'}$ are as defined for formulae (Ia) and (IIa) respectively; and
$R^{2'}$, $R^3$, $R^{4'}$, m1, n1, m2 and n2 are as defined above for formulae (III) and (IV) respectively, the monomer residues being arranged in any order.

The copolymers of and used in the method and composition of the invention are generally random (statistical) copolymers i.e. the precise structure will depend on the respective reactivity of the particular monomers used, the proportions of the monomers and the reaction conditions.

Generally the relative proportions of unsaturated ester and (sodium) styrene sulphonate used in the copolymer are from about 1:about 99 to about 99:about 1, more usually from about 10:about 90 to about 90:about 10 and advantageously from about 40:about 60 to about 60:about 40, by weight.

The weight average molecular weight of the copolymer of and used in the invention is 10 to 1000, more preferably 50 to 250 kilo-Daltons (kDa). This corresponds to an average number of repeat units of ester (when derived from monocarboxylic acid esters)—corresponding to the index m1 and m1' in the formulae (III) and (IIIa) above, of typically 10 to 200, more usually 10 to 150, and particularly 15 to 75, and of styrene sulphonate monomer i.e.—corresponding to the index n1 and n1' in the formulae (III) and (IIIa) above of typically 50 to 2500, more usually 100 to 2000, and particularly 150 to 750; and to an average number of repeat units of ester (when derived from dicarboxylic acid esters)—corresponding to the index m2 and m2' in the formulae (III) and (IIIa) above, of typically 10 to 250, more usually 10 to 150, and particularly 15 to 75, and of styrene sulphonate monomer i.e.—corresponding to the index n2 and n2' in the formulae (III) and (IIIa) above of typically 50 to 2000, more usually 100 to 1500, and particularly 200 to 1200.

In the hair care compositions of the invention, the copolymers, particularly of the formula (III) and (IV) above are generally used as aqueous based solutions in combination with other conventional formulation components such as organic solvents, surfactants, conditioning agents, thickeners, solubilisers, styling polymers, botanical extracts, UV-filters, preservatives and/or fragrances. Typically, hair treatment formulations will include both preservative and fragrance and will commonly include at least one of the other typical formulants listed above. In particular, the hair care composition is in the form of a hairspray, hair spritz, hair gel, hair colouring product, hair sunscreen product, shampoo, conditioner, styling mousse or gel, or other hair treatment composition. Advantageously the composition is in the form of an aqueous "leave on" composition or an aqueous "rinse off" composition.

In the hair care compositions of the invention, the copolymer of the styrene sulphonate and the unsaturated ester, particularly being or including the copolymer of the invention, desirably comprises from about 0.5 to about 25%, more desirably about 0.5% to about 10%, by weight of the hair care composition. Lower amounts generally do not give significant thermal protection to treated hair and higher proportions do not seem to give rise to additional benefit when the hair care formulations are applied to hair at normal application rates.

The composition of the invention is typically applied to hair in a generally conventional manner with the copolymer present in solution in an aqueous formulation. The application to hair will generally follow normal practice for the formulation type e.g. as a hairspray, hair spritz, hair gel, hair colouring product, hair sunscreen product, shampoo, conditioner, styling mousse or gel, or other hair treatment composition. And may be left on the hair after treatment or rinsed off. As the composition will usually be applied to provide improved protection from heat, the hair will then usually be subjected to a heat treatment e.g. drying, or styling. The effect of the treatment will usually be (or be measured as) a reduction in the average increase in the combing force (peak force or total work) after heat treatment of a treated tress of hair compared to an untreated tress of hair after heat treatment.

Figure 2:
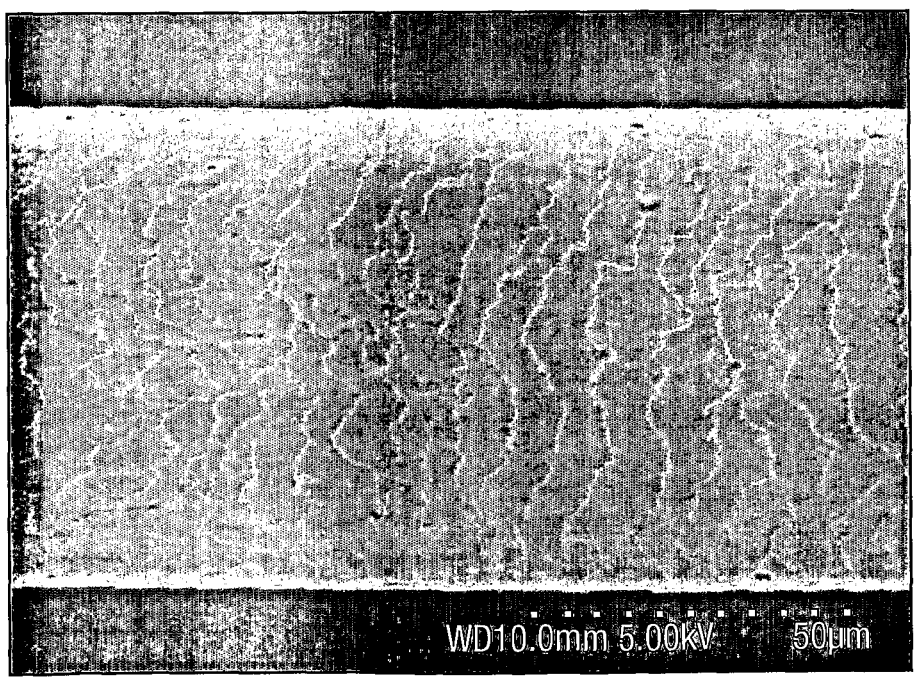
Figure 3:

FIGS. 1 to 3 illustrate the invention

FIG. 1 is a diagrammatic picture of testing tresses of hair using a tensile measurement device (see also below in the Examples). The testing method involves driving a comb through a tress of hair and the load required to achieve this is measured and peak forces and work done can be calculated. Referring to FIG. 1: a tress of hair (11) is clamped at one end into the machine (10) and a mechanical comb (12) is passed through the hair tress in the direction of arrow "A" whilst the force required to move the comb is measured by a measurement sensor (13).

Figure 4:
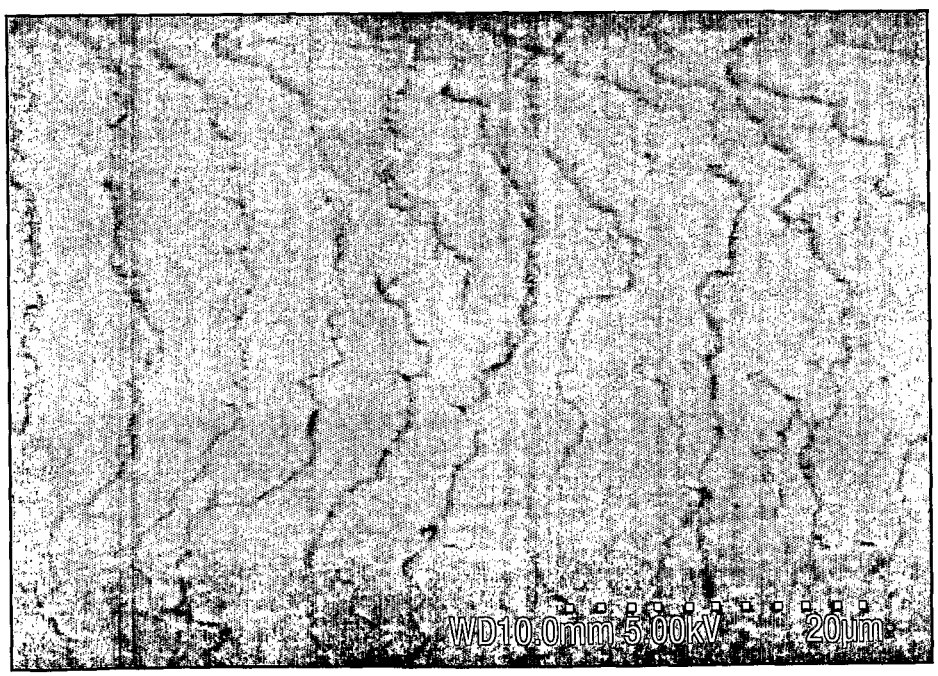

FIGS. 2, 3 and 4 are micrographs of hair. FIG. 2 shows untreated undamaged hair—the hair cuticles are smooth. FIG. 3 shows hair that has been damaged by heat treatment showing the raising of the cuticles and blisters on individual hair fibres which causes friction between the fibres, therefore making it more difficult to comb and so increasing the force required to comb the hair. FIG. 4 shows hair treated with a copolymer of this invention (SE1 below) and then heat treated in a similar fashion to the hair shown in FIG. 3. It will be noted that FIG. 4, which has 10 scale intervals indicating 20 μm, is at about 2.5 times the magnification of FIGS. 2 and 3, which have 10 scale intervals indicating 50 μm. The lower level of damage to the hair in FIG. 4 as compared with that shown in FIG. 3 is readily apparent.

The following Examples illustrate the invention. All parts and percentages are by weight unless otherwise stated.

| Materials | |
|---|---|
| Alcohols | |
| Alc1 | Laneth-40 ethoxylated lanolin alcohols; Polychol-40 ex Croda Chemicals Europe |
| Alc2 | cetyl/stearyl(C16/18) alcohol 25EO; Volpo CS25 ex Croda Chemicals Europe |
| Alc3 | methanol |
| Alc4 | ethanol |
| Alc5 | iso-propanol |
| Alc6 | butanol |
| Alc7 | cyclohexanol |
| Alc8 | propylene glycol |
| Alc9 | methoxy PEG 750 ex Croda Chemicals Europe |
| Acids | |
| UA1 | maleic acid |
| UA2 | fumaric acid |
| UA3 | acrylic acid |
| UA4 | methacrylic acid |
| Other | |
| NASS | sodium styrene sulphonate, Spinomar NaSS ex Honeywill & Stein Ltd |
| Init1 | 2,2'-azobis(2-amidinopropane) dihydrochloride, Wako V50; Wako Chemicals USA |

Test Methods

Acid Values (AV) were measured using a method based upon BS 684 Section 2.10 (1976) and results are quoted in mg(KOH)·g$^{-1}$ (sample)

Hydroxyl Values (OH) were measured using a method based upon BS 684 Section 2.9 (1976) and results are quoted in mg(KOH)·g$^{-1}$ (sample) and are corrected for the contribution of acid OH groups Saponification Values (Sap) were measured using a method based upon BS 684 Section 2.6 (1976) and results are quoted in mg(KOH)·g$^{-1}$ (sample)

Copolymer colour (Gdnr) was measured with a Dr Lange LICO 400 Colorimeter using a method based upon BS 6782 Part 5 (1977) and results are given as Gardner units

SYNTHESIS EXAMPLES

Example SE1

Laneth 40 Maleate/Sodium Polystyrene Sulphonate Copolymer

Alc1 (1360.7 g; 0.85 mol [based on the OH value of the Alc1]), UA1 (50.0 g; 0.43 mol) and hypophosphorous acid (8.5 g 50% w/w aqueous solution; 0.064 mol) were charged to a flanged flask and heated to 170° C. with stirring under nitrogen and water was distilled off until an acid value of <10 mg(KOH)·g$^{-1}$ was obtained. The reaction mixture was cooled to 65° C. to yield a mixture of mono- and di-(ethoxylated lanolin alcohol) esters of maleic acid.

A portion of this mixture of esters (96.0 g; ca 36 mmol) was dissolved in water (1073 g) at 80° C. and on complete dissolution, the solution temperature was reduced to 60° C.; the pH was adjusted to between 7.5 and 8.5 using aqueous NaOH (ca. 3.4 g of a 25% w/v solution); sodium styrene sulphonate (96.0 g; 430 mmol) added, followed by an aqueous solution of Init1 (4.4 g dissolved in 84 g water) at an even rate over a three hour period maintaining the reaction temperature at 60° C. The solution was stirred for a further hour, cooled to 50° C., the pH adjusted to between 4.5 and 5.0 using aqueous HCl (ca. 2.2 g 28% w/v solution), allowed to cool to ambient temperature and was then filtered to give the product copolymer as a clear, yellow, viscous liquid solution.

Examples SE2-SE13

Further synthesis Examples were carried out using the general method described in Example 1 but varying the acid and alcohol components of the unsaturated ester and the proportions of monomers in the copolymerisation. The materials and conditions used and the properties of the esters and copolymers are set out in Table SE1 below (including SE1):

TABLE SE1

| | Unsaturated esters | | | | | | Copolymers | | | |
|---|---|---|---|---|---|---|---|---|---|---|
| Ex No | Acid | Alcohol | ratio | AV | OH | Sap | wt ratio | pH | % solids | Colour |
| SE1 | UA1 | Alc1 | 1:2 | 9.7 | 13.1 | 26.6 | 50:50 | 8.0 | 16.0 | 4.6 |
| SE22 | UA1 | Alc2 | 1:2 | 9.4 | 18.1 | 29.7 | 50:50 | 8.0 | 14.1 | 0.5 |
| SE3 | UA1 | Alc3 | 1:2 | 1.8 | 0 | 77.39 | 3:97 | 8.0 | 13.7 | 0.3 |
| SE4 | UA1 | Alc4 | 1:2 | 8.7 | 248.0 | 203.2 | 50:50 | 8.0 | 8.2 | 1.0 |
| SE5 | UA1 | Alc5 | 1:2 | 10.0 | 254.8 | 271.4 | 50:50 | 8.0 | 7.5 | 9.9 |
| SE6 | UA1 | Alc6 | 1:2 | 1.3 | 92.6 | 270.6 | 50:50 | 8.0 | 7.4 | 8.0 |
| SE7 | UA1 | Alc7 | 1:2 | 9.3 | 95.4 | 284.7 | 50:50 | 8.0 | 8.1 | 8.7 |
| SE8 | UA1 | Alc8 | 1:2 | 9.6 | 174.7 | 331.5 | 50:50 | 8.0 | 12.8 | 6.3 |

TABLE SE1-continued

| | Unsaturated esters | | | | | | Copolymers | | | |
|---|---|---|---|---|---|---|---|---|---|---|
| Ex No | Acid | Alcohol | ratio | AV | OH | Sap | wt ratio | pH | % solids | Colour |
| SE9 | UA1 | Alc9 | 1:2 | 3.0 | 0.6 | 84.5 | 50:50 | 8.0 | 13.9 | 0.6 |
| SE10 | UA1 | Alc9 | 1:2 | 9.7 | 30.7 | 44.2 | 50:50 | 8.0 | 14.0 | 3.4 |
| SE11 | UA1 | Alc9 | 1:2 | 9.7 | 30.7 | 44.2 | 15:85 | 8.0 | 14.5 | 1.7 |
| SE12 | UA2 | Alc1 | 1:2 | 14.8 | 23.3 | 33.0 | 50:50 | 8.0 | 14.4 | 2.4 |
| SE13 | UA3 | Alc1 | 1:1 | 0.5 | 25.1 | 11.2 | 50:50 | 8.0 | 14.4 | 2.6 |
| SE14 | UA3 | Alc1 | 1:1 | 2.1 | 26.0 | 21.4 | 50:50 | 8.0 | 14.7 | 5.8 |
| SE15 | UA4 | Alc1 | 1:1 | 4.3 | 27.2 | 10.7 | 50:50 | 8.0 | 14.0 | 4.5 |

APPLICATION EXAMPLES

| Materials | |
|---|---|
| Polymers | |
| Copolymers of the invention are designated by the respective SE Nos | |
| CPol1 | poly(sodium styrene sulphonate); Flexan II ex National Starch |
| CPol2 | vinyl pyrrolidone dimethylaminopropyl methacrylate copolymer; Styleze CC-10 ex ISP |
| Other | |
| ethanol | DEB 100 ex Charles Tennant & Co |
| HEC | aqueous hydroxyethyl cellulose solution (2% w/v); Natrasol ex Hercules |

Combing Study Protocol

The damage caused to tresses of test hair by straightening irons was assessed by measuring the force required to comb through a tress of hair (pre-tressed European brown hair) using the Dia-Stron MTT 175 Miniature Tensile Tester (Dia-Stron Ltd of Andover, Hampshire, UK, SP10 5NY) as illustrated in FIG. 1 using the following operating conditions:

| Standard Dia-Stron MTT 175 Operating Conditions | |
|---|---|
| Range: | 400.0 g (force) |
| Gauge: | 0.0 g (force) |
| Speed: | 120 mm · min$^{-1}$ |
| Number of cycles | 1 |

This instrument and method was developed for hair care applications and for the evaluation of efficacy of shampoos and conditioners. In the method a comb is driven through a tress of hair and the load required to achieve this is measured and peak forces and work done can be calculated. Referring to FIG. 1: a tress of hair (11) is clamped at one end into the machine (10) and a mechanical comb (12) is passed through the hair tress in the direction of arrow "A" whilst the force required to move the comb is measured by a measurement sensor (13).

The damage caused by heat treatments includes raising the cuticles on the individual hair fibres (as shown in FIGS. 2 and 3) causing friction between the fibres, therefore making it more difficult to comb and so increasing the force required to comb the hair.

Test Procedure

Baselines Data Measurements

Separately each hair tress was slowly dipped into 2000 ml of water (at ambient temperature) three times to allow it to regain its natural conformation; then squeezed through the fingers twice to remove excess water; combed using the Dia-Stron MTT 175, under the standard set of conditions, (detailed above), and the peak combing value and total work recorded. These steps were repeated a further two times to give three readings. The results were analysed to give the total work and peak combing force (averaged as "B").

Hair Treatment Procedure

Each test tress was sprayed 3 times on each side, whilst wet, with a test non-aerosol heir spray; combed through to ensure even coverage; blow dried for 3 minutes and combed through; then straightened for 30 seconds with the straightening irons held stationary, 90 mm from the top of the tress.

Measurement

Each sprayed and dried tress was treated and measured as described for the baseline measurement above and the total work and peak combing force (averaged as "S") was recorded for a total of three runs.

The effect of the treatment on increase in combing force after the heat treatment was calculated using Equation 1 (below) to give the average change in combing force as a percentage:

$$\text{Average change in combing force} = \frac{(S-B)}{B} \times 100\% \quad \text{Equation 1}$$

Where:
S=the force required to comb the hair measured after straightening
B=the baseline force measured before straightening The average percentage change in combing force was calculated for each tress. 10 repeats of the procedure were carried out and the average percentage change in peak force and total work required to comb the hair for each product was calculated. The data was observed to be normally distributed and so was analysed using the parametric test, the unpaired student t-test to determine the statistical significance of the results.

Example AE1

Combing Study to Assess the Heat Protection Properties of Various Polymers

A base aqueous/alcoholic non-aerosol hair spray formulation was made up by mixing the following components:

| | wt % |
|---|---|
| Ethanol DEB 100 | 30 |
| HEC (2% solution) | 5 |
| Triethanolamine | to pH 6.0 |
| Active under test | qs (to provide 0.5% of active) |
| Water | to 100 |

Tresses of European brown hair 15 mm wide and 240 mm long were cut and labelled. Each tress was washed with 10% aqueous sodium laureth sulphate (SLES) solution to ensure cleanliness. The test procedure was carried out using sprays as described above with no test active (AE1.Base) and copolymers SE1 (AE1.1) and SE11 (AE1.2); and polymers CPol1 (AE1.C1) and CPol2 (AE1.C2) as test actives. The results, including p-values from significance testing, are shown in Table AE1 below.

TABLE AE1

| Ex No | Test Active | Property change | | | |
|---|---|---|---|---|---|
| | | TW (%) | p-value | PF (%) | p-value |
| AE1.Base | none | 148.7 | n/a | 170.8 | n/a |
| AE1.1 | SE1 | 50.9 | 0.038 | 50.6 | 0.085 |
| AE1.2 | SE11 | 41.2 | 0.022 | — | — |
| AE1.C1 | CPol1 | 127.0 | 0.659 | 171.1 | 0.997 |
| AE1.C2 | CPol2 | 94.8 | 0.277 | 116.1 | 0.474 |

The results show that tresses treated with the copolymer of SE1 or SE11 gave significantly lower increases in both total work and peak force in the combing study compared to the two commonly used polymeric cosmetic heat protection agents. This leads to the conclusion that the copolymers of SE1 and SE11 impart significantly more heat protection to hair during cosmetic use than the two comparison polymers.

The invention claimed is:

1. A method of providing a thermal-protective or styling-protective hair treatment, comprising:
   applying to hair a composition comprising about 0.5 wt. % to about 10 wt. % of at least one copolymer consisting of at least one unsaturated ester and a styrene sulphonate monomer, wherein the composition reduces hair damage caused by subsequent heat treatment or styling.

2. The method of claim 1, wherein the at least one unsaturated ester comprises:
   i) a residue of a monocarboxylic acid or an unsaturated dicarboxylic acid; and
   ii) a reside of an alcohol.

3. The method of claim 1, wherein the at least one unsaturated ester comprises a residue of an unsaturated dicarboxylic acid and a reside of an alcohol.

4. The method of claim 2, wherein the alcohol is one or more of:
   i) a $C_{12}$ to $C_{35}$ alcohol, comprising a straight chain alcohol, a branched chain alcohol, a cyclic alcohol, an aromatic alcohol, a fatty alcohol, a sterol, a stanol, an alcohol derived from woolgrease, a lanolin alcohol, a diol, a polyol, or an alkoxylated or (poly)alkoxylated alcohol;
   ii) an alkoxylated alcohol; or
   iii) a (poly)alkoxylated alcohol.

5. The method of claim 4, wherein the (poly)alkoxylated alcohol comprises 1 to 100 moles of the alkoxylating moiety(s) per mole of alcohol.

6. The method of claim 5, wherein the alkoxylating moiety is one or more of an ethyleneoxy, polyethyleneoxy, propyleneoxy, polypropyleneoxy, or a mixture of two or more of these.

7. The method of claim 6, wherein the alcohol is ethoxylated lanolin alcohol.

8. The method of claim 2, wherein the monocarboxylic acid or dicarboxylic acid is one or more of an ethylenically unsaturated or an $\alpha,\beta$-unsaturated carboxylic acid.

9. The method of claim 8, wherein the monocarboxylic acid is one or more of acrylic acid, methacrylic acid, crotonic acid, 3-methylcrotonic, 3-butenoic acid, or a mixture of two or more of these.

10. The method of claim 8, wherein the dicarboxylic acid is one or more of maleic acid, fumaric acid, itaconic acid, citraconic acid, mesaconic acid, or a mixture of two or more of these.

11. The method of claim 10, wherein the dicarboxylic acid is maleic acid.

12. The method of claim 11, wherein the alcohol is ethoxylated lanolin alcohol.

13. The method of claim 1, wherein the styrene sulphonate monomer is styrene sulphonate, or a neutralized salt thereof.

14. The method of claim 13, wherein the salt is an alkali metal or an amine salt.

15. The method of claim 14, wherein the alkali metal is sodium.

16. The method of claim 2, wherein the styrene sulphonate monomer is sodium styrene sulphonate.

17. The method of claim 16, wherein the dicarboxylic acid is one or more of maleic acid, fumaric acid, itaconic acid, citraconic acid, mesaconic acid, or a mixture of two or more of these.

18. The method of claim 1, wherein the styrene sulphonate monomer is sodium styrene sulphonate.

19. The method of claim 18, wherein the dicarboxylic acid is one or more of maleic acid, fumaric acid, itaconic acid, citraconic acid, mesaconic acid, or a mixture of two or more of these.

20. The method of claim 1, wherein the copolymer contains from about 1 to about 99 parts by weight of residues of unsaturated ester and about 99 to about 1 parts by weight of residues of the styrene sulphonate monomer.

21. The method of claim 1, wherein the copolymer contains from about 10 to about 90 parts by weight of residues of unsaturated ester and about 90 to about 10 parts by weight of residues of the styrene sulphonate monomer.

22. The method of claim 1, wherein the copolymer contains from about 40 to about 60 parts by weight of residues of unsaturated ester and about 60 to about 40 parts by weight of residues of the styrene sulphonate monomer.

23. The method of claim 1, wherein the copolymer comprises from about 0.5% to about 10% by weight of the composition.

24. The method of claim 1, wherein the composition is in the form of a hairspray, hair spritz, hair gel, hair coloring product, hair sunscreen product, shampoo, conditioner, styling mousse or gel, or other hair treatment composition.

25. The method of claim 1, wherein the composition is in the form of an aqueous "leave on" composition or an aqueous "rinse off" composition.

26. The method of claim 1, wherein the thermal protection provided by the composition manifests itself as a reduction in the average percentage increase in the combing force after heat treatment of a treated tress of hair compared to an untreated tress of hair after heat treatment.

27. The method of claim 1, wherein the method further comprises styling the treated hair, wherein the styling causes less hair damage to the treated styled-hair relative to untreated styled-hair.

28. The method of claim 1, wherein the method further comprises heating the treated hair, wherein the heating causes less hair damage to the treated heated-hair relative to untreated heated-hair.

29. The method of claim 16, wherein the monocarboxylic acid is one or more of acrylic acid, methacrylic acid, crotonic acid, 3-methylcrotonic, 3-butenoic acid, or a mixture of two or more of these.

* * * * *